US008732002B2

(12) United States Patent
Previdi

(10) Patent No.: US 8,732,002 B2
(45) Date of Patent: May 20, 2014

(54) APPARATUS AND METHOD FOR REWARDING CONSUMERS

(76) Inventor: Robert G. Previdi, Morristown, NJ (US)

( * ) Notice: Subject to any disclaimer, the term of this patent is extended or adjusted under 35 U.S.C. 154(b) by 642 days.

(21) Appl. No.: 12/256,144

(22) Filed: Oct. 22, 2008

(65) Prior Publication Data

US 2009/0094062 A1    Apr. 9, 2009

Related U.S. Application Data

(63) Continuation of application No. 10/863,176, filed on Jun. 8, 2004.

(51) Int. Cl.
*G06Q 30/00* (2012.01)

(52) U.S. Cl.
USPC ............................................. 705/14

(58) Field of Classification Search
USPC ............................................. 705/14
See application file for complete search history.

(56) References Cited

U.S. PATENT DOCUMENTS

| | | | |
|---|---|---|---|
| 5,128,752 A | 7/1992 | Von Kohorn | |
| 5,832,449 A | 11/1998 | Cunningham | |
| 6,101,483 A | 8/2000 | Petrovich et al. | |
| 6,112,182 A | 8/2000 | Akers et al. | |
| 6,189,787 B1 | 2/2001 | Dorf | |
| 6,256,614 B1 | 7/2001 | Wecker et al. | |
| 6,502,745 B1 | 1/2003 | Stimson et al. | |
| 7,640,177 B2 | 12/2009 | Fralic | |
| 2002/0107717 A1 | 8/2002 | Liu et al. | |
| 2002/0128898 A1 | 9/2002 | Smith, Jr. et al. | |
| 2003/0070338 A1 | 4/2003 | Roshkoff | |
| 2003/0212577 A1* | 11/2003 | Nichtberger | 705/2 |
| 2003/0236704 A1 | 12/2003 | Antonucci | |
| 2003/0236712 A1 | 12/2003 | Antonucci et al. | |
| 2005/0222904 A1* | 10/2005 | Cotten et al. | 705/14 |
| 2005/0228692 A1 | 10/2005 | Hodgdon | |
| 2006/0085231 A1 | 4/2006 | Brofman | |
| 2006/0161453 A1* | 7/2006 | Kost et al. | 705/2 |
| 2006/0190337 A1* | 8/2006 | Ayers et al. | 705/14 |
| 2007/0233526 A1 | 10/2007 | Hoffman et al. | |

OTHER PUBLICATIONS

Reprinted With the Permission From Computer Talk for the Pharmacist, May/Jun. 2004, OPUS Health: Moving Samples to the Pharmacy, Hauppauge, NY, pp. 5 and 6.
National Council for Prescription Drug Programs (NCPCP), Telecommunication Standard Format Version 5 Release 1,Sep. 1999, Scottsdale, AZ.

\* cited by examiner

*Primary Examiner* — Alvin L Brown
(74) *Attorney, Agent, or Firm* — George R. McGuire; Blaine T. Bettinger; Bond Schoeneck & King, PLLC

(57) ABSTRACT

In order to reward a consumer for trying or learning about a product, the customer is given a unique identification number, preferably an unvalidated ATM readable card, and instructions for completing a test or survey by telephone or on the Internet. Upon successful completion of the test by the consumer, the identification number is validated so that the consumer may withdraw a cash reward from a temporary bank account funded when the identification number is validated via an ATM. Where the consumer is the patient of a physician, the patient may receive the number and card from the physician along with a prescription for redemption at a pharmacy whereat the pharmacy dispenses a supply of the drug to the patient and is paid by the manufacturer of the drug through the former's insurance payment processing system.

10 Claims, 4 Drawing Sheets

APPARATUS AND METHOD FOR REWARDING CONSUMERS

CROSS REFERENCE TO RELATED APPLICATION

The present application is a continuation of and claims priority to Applicant's co-pending U.S. patent application Ser. No. 10/863,176, filed Jun. 8, 2004.

BACKGROUND OF THE INVENTION

The present invention relates to apparatus for, and a method of inducing a consumer to use or learn about a product by providing a reward for his or her doing so. More specifically, the present invention teaches apparatus and a method for providing the consumer with a reward card which can be conveniently used by the consumer to timely obtain the reward after the consumer has purchased the product or completed a test or survey relating to it.

It is known in the art to reward a customer for taking a survey by electronically crediting an account accessible to the customer. Such a method is disclosed in U.S. Patent Publication No. 20020128898 by Smith et al. for Dynamically Assigning a Survey to a Respondent. However, such a system requires the consumer to disclose his or her personal credit card number or Internet service account number so that it may be credited with the reward. Consumer's are reluctant to make such disclosures in view of concerns as to fraud and identity theft which in current times present real risks. Smith et al. do not disclose the use of a reward card as a means of enabling the customer to redeem a reward.

U.S. Patent Publication No. 20020107717 A1 to Liu et al. provides for reward payments to participants in a survey who use a credit card at a point-of-sale or point-of-transaction terminal. While a user of a credit card is paying for a purchase or service, a survey is presented to the user. As a reward for completing the survey, money is credited to the user's credit card account, or miles may be credited to the user's airline mileage account.

U.S. Pat. No. 6,502,745 to Stimson, et al. for a Pre-Paid Card System and Method discloses a system and method for taking surveys when a prepaid card, e.g., a calling card, is used. At the time the card is inserted into a card reader, the user may be asked to participate in a survey which is conducted at the card reading device. The user can be rewarded by adding additional value to the card, e.g., additional minutes if the card is a telephone calling card.

U.S. Pat. No. 6,256,614 to Wecker, et al. for an Internet System For Producing Electronic Reward Cards discloses a system for rewarding consumers who take a survey on the Internet. The reward is given by issuing a new card or adding value to an existing card.

U.S. Patent Publication No. 20030236704 for a System and Method for a Multiple Merchant Stored Value Card, and U.S. Patent Publication No. 20030236712 for a System and Method for Distributing Vouchers, both by Antonucci, are directed to a system for awarding loyalty points to consumers. A participating consumer may earn loyalty points by completing an online survey. Loyalty points issued for redemption at different merchants can be tracked in a single database tied to a single transaction card.

U.S. Pat. No. 6,189,787 to Dorf for a Multifunctional Card System also discloses a card which can be used to receive and spend value of various types, from different merchants, e.g., airline miles, telephone minutes, and money.

U.S. Pat. No. 5,128,752 to Von Kohorn for a System and method for generating and redeeming tokens discloses a reward system which utilizes an appliance connected to a television set for generating rewards in the form of tokens or coupons.

The prior art methods require a consumer to take a test or survey at the time that the reward is offered, and through the consumer's own bank or credit card account whereby the consumer's responses are associated with his or her identity. In addition to the consumer's identity, his or her bank or credit card accounts must also be disclosed to obtain a reward. None of the prior art approaches to rewarding consumers for using a product, or learning about the product, or taking a test or survey provides a consumer with a time deferred and anonymous way of obtaining a reward for his or her doing so.

SUMMARY OF THE INVENTION

The present invention teaches apparatus for and a method of getting a person to provide information to a vendor and, in return, rewarding him with a reward card which looks and works somewhat like a debit card and from which a cash or merchandise reward can be obtained.

Typically the person is a consumer who is asked to complete a survey, or to read the manufacturer's promotional literature and then take a test. According to the method of the invention, a consumer is given a "not yet validated" reward card having an identification number which is embossed on the front of the card and also encoded in a magnetic stripe on the back of the card. The consumer, thereafter, dials a telephone number on the card to take the test or participate in a survey. If a test is to be taken, the consumer may have been given a brochure to read about a manufacturer's product. The test will determine whether the consumer has read the brochure.

While taking the test or participating in the survey by telephone, the consumer will be asked questions to which he or she may respond by pressing telephone buttons to generate touch tones, or may give voice responses, i.e., "yes" or "no" to an interactive voice response system (IVR).

Funds sufficient to pay all participating consumers are kept in a bank account of the manufacturer. If the test or survey is properly completed by the consumer, the identifier on the card is "validated" and, simultaneously, there is created a temporary bank account associated with the number on the consumer's card which is funded by transferring from the manufacturer's bank account to the temporary account, funds sufficient to pay the reward, e.g. $20.00. The consumer may then insert the card into any ATM in the banking system and receive a cash reward from the temporary account.

Alternatively, provision may be made to use the card as a debit card to make a purchase in a store. In a variation of the above, the card may be redeemable for merchandise instead of cash. If the manufacturer is a pharmaceutical manufacturer, the card may be used to obtain free prescription medication from a pharmacy. Instead of processing the transaction through a bank, the pharmacy may enter the number on the card into its insurance payment processing system to obtain payment for the "free medicine" that is being provided to the consumer who presents the card. For example, the pharmacy may have a point of sale (POS) terminal with a card reader which can interpret the identifier on the reward card and determine whether it has been validated, i.e., whether an account with an insurance company accessible via the pharmacy's insurance payment processing system has been funded.

Also, where a test is taken, the reward may vary with the number of correct answers, e.g., $20 for 5 correct answers to 10 questions versus $50 for 10 correct answers to 10 questions.

The card may be distributed with free samples of a product, e.g., medicine, and may be redeemable for more free product after the test or survey is completed.

DESCRIPTIONS OF THE DRAWINGS

DESCRIPTION OF THE PREFERRED EMBODIMENT

Figure 1:
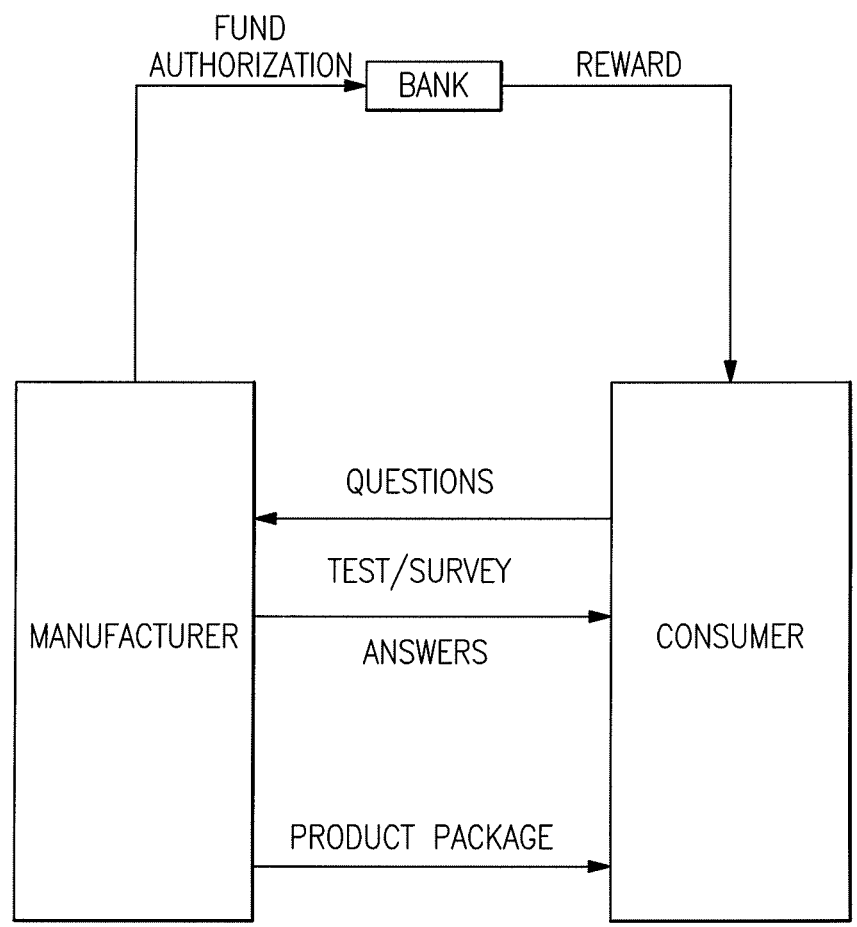
FIG. 1 is a schematic block diagram of a method of a first embodiment of the invention.

Referring now to FIG. 1 of the drawings, in accordance with the invention, a manufacturer prepares product packages for distribution to consumers whom the manufacturer wants to become customers for the product and/or from whom the manufacturer wishes to acquire information from the consumer. Included in each product package is an unvalidated reward card which the consumer may use to redeem a cash reward from a bank once the card is validated. Also to be found within the product package is information to direct and enable the consumer to take a test or survey prepared by the manufacturer in order to enable the consumer to qualify for the reward.

If the consumer completes the test or survey in a manner which meets predetermined criteria established by the manufacturer for earning the reward, the manufacturer authorizes its bank to set up and fund from the manufacturer's bank account, a temporary bank account associated with an identification number assigned to the consumer. The consumer may then withdraw the reward from the assigned and funded temporary bank account, preferably by using the card in an automatic teller machine (ATM).

Figure 2:
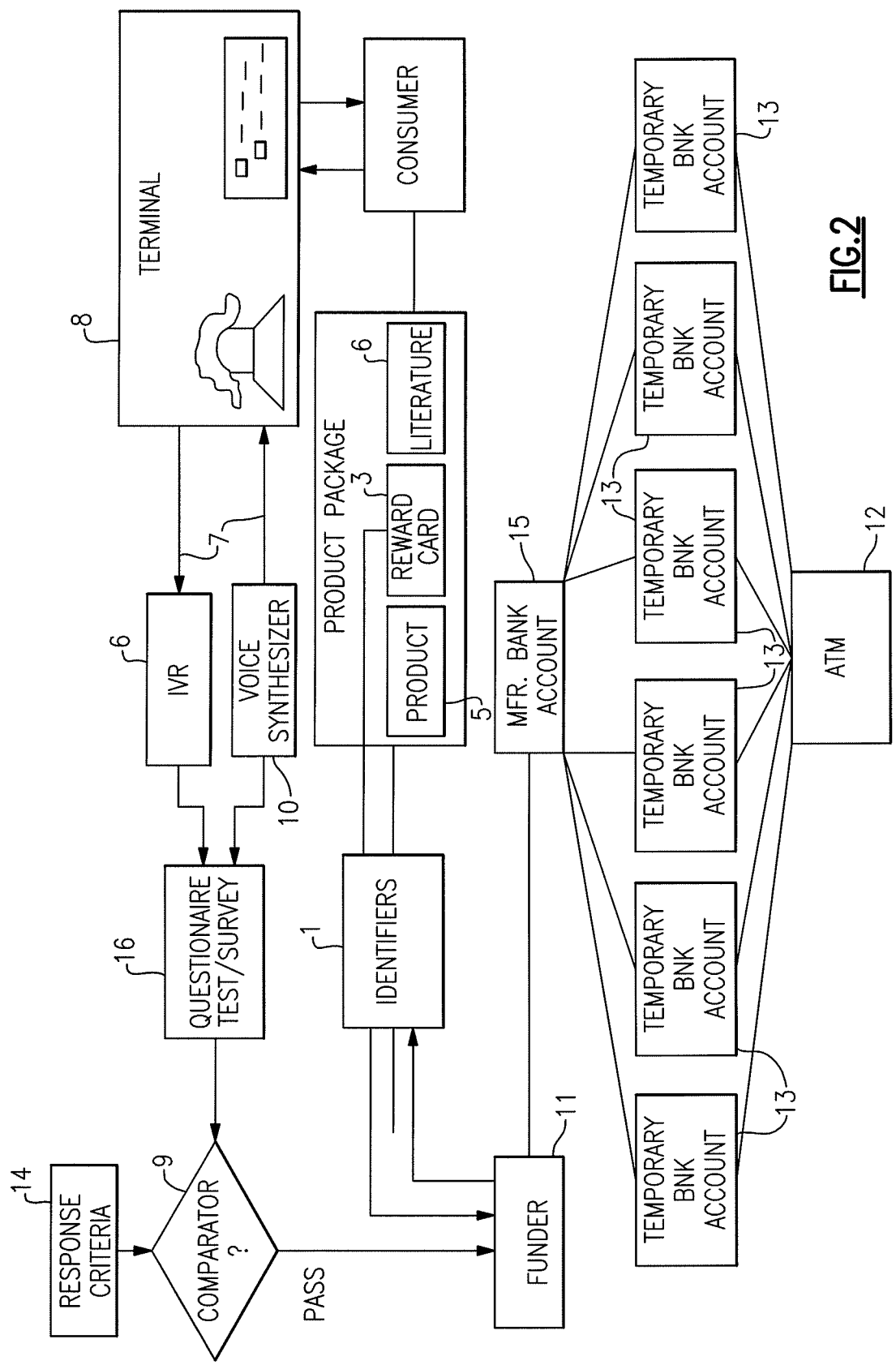
FIG. 2 is a schematic block diagram of apparatus for performing the method of FIG. 1.

Referring additionally to FIG. 2 of the drawings, identification numbers, each of which is unique, are entered into fields within respective records of a table in a database stored as a computer file, preferably on a non-volatile electronically readable computer storage device 1 such as a magnetic or optical disk drive or a magnetic tape drive. A validation field is provided in each record to indicate whether the identification number has been validated as a result of a consumer having successfully completed a survey or a test.

Such a survey will normally be fashioned to enable a product manufacturer to acquire statistical data which can be analyzed to derive information that will aid in marketing its products. A product manufacturer seeking to educate consumers about its products in the hope of making them customers for the products may package with a product 5 offered for sale to the consumer, or given for free as a promotional sample, literature 6 explaining the benefits of or otherwise promoting the product 5. A test would then be used to verify that the consumer has read the literature.

In order to enroll a consumer in the reward program to which the apparatus and method of the invention are directed, the consumer is assigned one of the unique identification numbers. This is most conveniently done by giving the consumer a reward card 3 bearing the identification number. The reward card 3 is preferably packaged with a product 5 that is purchased by or otherwise given to the consumer. In addition to or instead of the identification number being imprinted or embossed on the reward card 3, the reward card 3 may be provided with a device for making the identification number machine readable. For example, where the reward card 3 is intended to be used for withdrawing a cash reward from an automatic teller machine 2 (ATM), the reward card 3 will have a magnetic stripe onto which the consumer's assigned identification number is encoded. Alternatively, the reward card 3 may have imbedded within it a radio-frequency identifier (RFI) circuit or other machine readable device.

In accordance with the invention, the reward card 3 bearing the identification number is packaged with instructions for making contact with a bidirectional communication link 7 to a computer which is programmed to administer the test or survey. The computer 7 may be the same as or separate from the computer in which the storage device 1 is installed for maintaining user identification numbers.

For example, the instructions packaged with the reward card 3 may invite the consumer to take the test or survey, and provide instructions for reaching the communication link 7 from a readily available communications terminal 8 such as a telephone, preferably but not necessarily a touch tone telephone. Upon dialing the number the consumer is greeted with a computer generated voice message, via a voice synthesizer 10, explaining the nature of the test and how to answer the questions by entering responses via the telephone's touch tone keypad. Where a touch tone keypad is to be used, the questions will preferably be of the multiple choice or true-false type. An interactive voice response system (IVR) 6 may be used to enable the computer to receive voice responses to the questions provided by the consumer.

The test or survey may also be administered over the Internet. In such a case, the uniform resource locator (URL) for a website established by the manufacturer is provided with instructions for using the reward card 3 to obtain a reward. Upon entering the URL, via a keyboard at the terminal 8, which is connected to a computer (not shown) programmed with commercially available Internet web browsing software, the consumer is presented with a page having instructions and links to questions for taking the test or survey. Responses to the questions can be entered online, recorded and scored by the manufacturer's computer, as will be known to those skilled in the art.

The computer containing the software for administering the test over a telephone line or on the Internet as previously explained, is programmed with software for evaluating the consumer's responses to the test or survey. The evaluation may be based in whole or in part on the number of correctly answered test questions, the total number of test or survey questions answered, the time spent completing the test or survey, consistencies among answers to related questions, or various other criteria indicative of whether the consumer made a good faith effort to read the accompanying literature, where applicable, or to provide requested information.

In a computer storage 14 which is a component of or accessible by the computer which evaluates the consumer's response to the test or survey are criteria for a successful completion of the test or survey, e.g., minimum number of correct answers. A comparison is made between the evaluation of the consumer's response to the test or survey 16 and the minimal criteria 14 for a successful completion of the test or survey 16 in a comparator 9 which can also be programmed in software. If the comparison determines that the minimal criteria for a successful completion of the test or survey have been met or exceeded, the comparator generates a "pass"

signal which is necessary to enable the consumer to receive his or her reward. The validation field in the data record for the consumer's identification number is then modified to indicate that the reward has been approved for a reward.

If the comparison determines that the minimal criteria for a successful completion of the test or survey have not been met, the comparator may generate a "fail" signal which causes the validation field in the record for the consumer's identification number to indicate disapproval of the reward, thereafter preventing the consumer from using the reward card 3 or identification number to obtain a reward. Alternatively, the computer may be programmed so that in the absence of a "pass" signal, the validation field is left neutral, that is, with the same contents that it had before the test or survey was administered thereby affording the consumer another opportunity to take the test or survey and obtain the reward.

A funder software module 11 queries the table of identification numbers, either periodically or on command, to determine which identification numbers have been approved for customer rewards. For each record having a value of "approved" in its validation field, in a scan of the identification number records in the database, the finding software module 11 sets up a temporary bank account 13, at the manufacturer's bank, which is linked to a master account 15 of the manufacturer.

The funding software module 11 then transfers from the master account 15 to the temporary account 13, funds equal to the amount of the reward to which the consumer is entitled for completing the test or survey.

The temporary account 13 is preferably made accessible via an ATM 2 into which the reward card 3 can be inserted for enabling withdrawal of the reward in cash, much the same as a bank credit or debit card may be used. Alternatively, the identification number may be included in a list accessible to a merchant of a product 5 which constitutes the reward, and from whom the consumer may obtain the reward by visiting the merchant.

Figure 3:
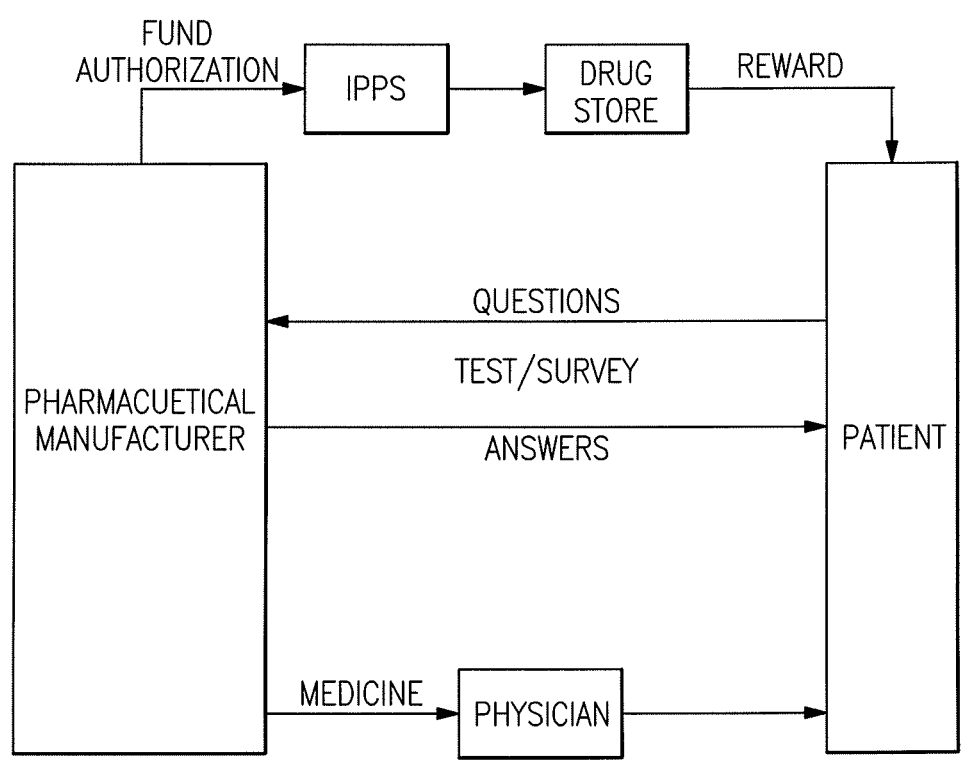
FIG. 3 is a schematic block diagram of a method of a second embodiment of the invention.

Referring now to FIG. 3 of the drawings, there is shown an alternative embodiment of the invention tailored for use with specific classes of consumers and products, namely medical patients who use prescription medicines. In this variation of the invention, the manufacturer may be a producer of a prescription drug for treating a specific ailment who is seeking to have patients try an initial, and possibly a follow-up, sample of the drug. In order to accomplish this, the manufacturer supplies physicians who treat the ailment with reward cards, drug literature, and/or drug samples at least one of which contains a unique consumer identification number. Reward cards, drug literature, and/or drug samples are provided to the physician free of charge so that the physician may pass along to a patient believed to possibly benefit from the drug, a reward card 3, drug literature, and/or drug sample, along with a prescription for a further supply of the drug.

The patient may be required to complete a survey or test as in the case where a monetary or product reward is given in connection with the promotion of a nonpharmaceutical product 5. In such a case, the patient's response to the survey or test may be evaluated as explained above, and an entry may be made in a database record for the patient's identification number indicating approval of the reward, i.e., the further supply of the drug. Alternatively, no test or survey may be required for obtaining a follow-up supply of the drug.

Instead of a bank account accessible through an ATM 2, the manufacturer of the drug would arrange for payment of pharmacies dispensing a sample of the drug to the patient through the insurance payment processing system (IPPS) used by each pharmacy. A card reader in the pharmacy's point of sale (POS) terminal could interpret the identifier number on the card and then obtain an authorization to provide the reward to the customer in the form of medication. The temporary insurance account established for funding the reward could then be accessed by the pharmacy for reimbursement.

Figure 4:
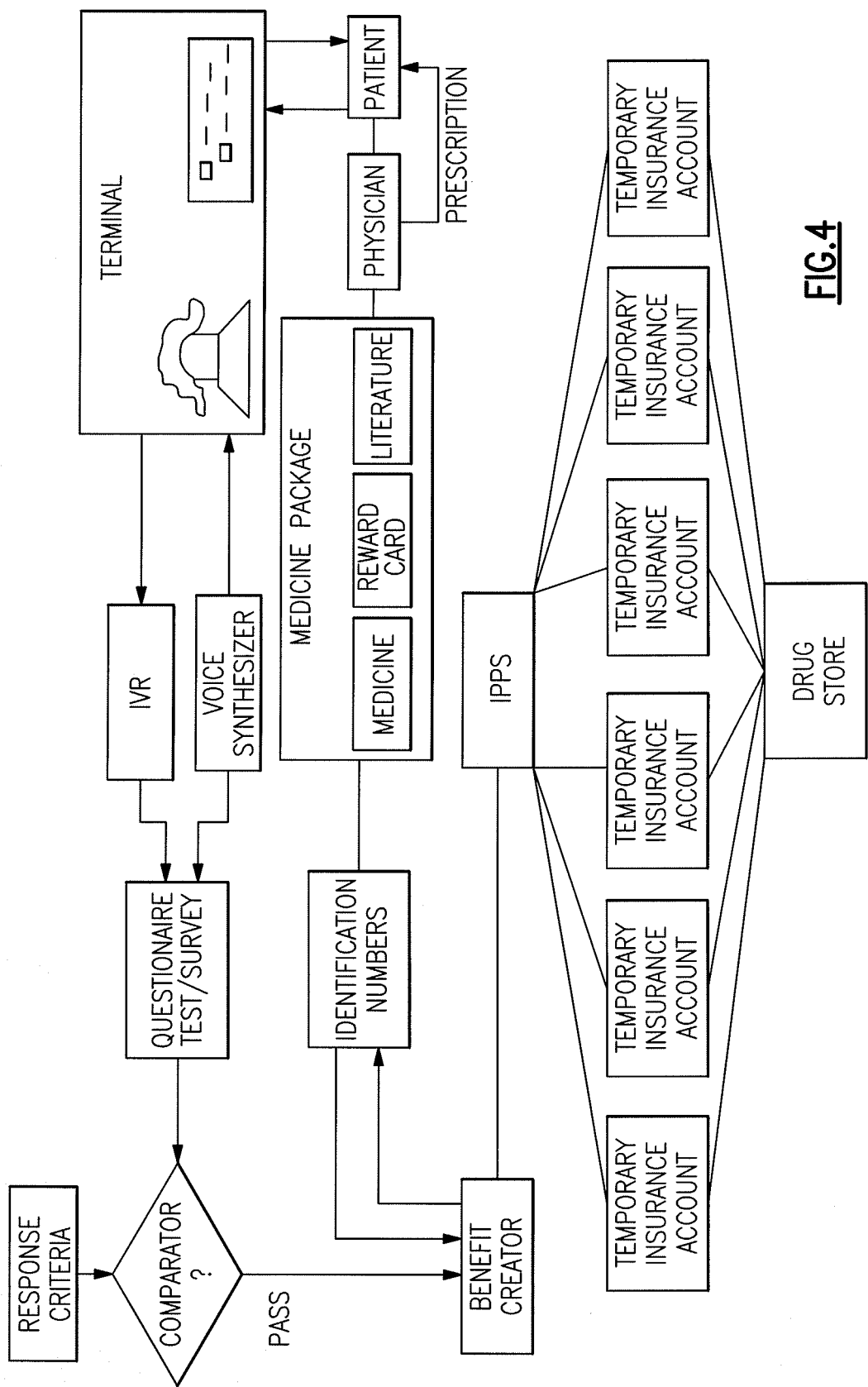
FIG. 4 is a schematic block diagram of apparatus for performing the method of FIG. 3.

Referring additionally to FIG. 4, upon approval of a reward, e.g., a drug sample, for a patient, a benefit creator, analagous in function to the funding software module 11 used to fund a cash reward, creates a temporary insurance account with a medical insurance provider or health maintenance organization (HMO) with whom the pharmaceutical manufacturer has made a payment arrangement. The pharmacist may then bill the insurance company or HMO for reimbursement for the cost of the reward medicine supply given to the patient, through its insurance payment processing system, just as it normally does with respect to customers who purchase medication covered by their insurance policies.

In addition to the normal charge for dispensing the medication, the pharmacy may also be paid a service fee as an incentive for participating in the manufacturer's promotional program. A monetary incentive to the pharmacy, beyond its normal profit on the prescription, would be particularly appropriate where the pharmacy is requested to obtain personal data from the patient with a consent to disclose it to the pharmaceutical manufacturer for use in communicating directly with the patient in order to learn of the effectiveness of the drug, the patient's attitude towards it, and any other information which may help the manufacturer in tailoring the drug and its distribution to enhance the effectiveness of the drug and or its profitability.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of distributing a prescription drug sample to a consumer through a pharmacy, the method comprising the steps of:

distributing to a drug prescriber at least one machine readable card, each of which is encoded with a unique identifier, and patient instructions for participating in a test or questionnaire;

inducing the drug prescriber to distribute to a patient, a prescription for said drug sample, said patient instructions, and at least one of said machine readable cards;

inducing said patient to follow said instructions to participate in a test or questionnaire;

funding, by a computer, a deposit account associated with said unique identifier, with an insurance company payment processing system, accessible by said pharmacy for obtaining payment for drugs dispensed to customers insured by an insurance company that pays claims through the insurance company payment processing system, in an amount sufficient to reimburse said pharmacy for its charge for said drug sample, wherein said deposit account is only funded upon successful completion of said test or questionnaire;

inducing said patient to present said machine readable card to said pharmacy with said prescription for obtaining said drug sample, and reimbursing said pharmacy from said funded deposit account for said charge for said drug sample in response to said card being read by a card reader linked to said insurance company payment processing system.

2. A method according to claim 1 further comprising, interpreting said unique identifier in response to said card being read by a card reader, and producing an authorization for reimbursing said pharmacy for said charge for said drug sample corresponding to said unique identifier before reimbursing said pharmacy for said charge for said drug sample.

3. A method according to claim 1 comprising, inducing said drug prescriber to distribute to said patient with said prescription for said drug sample and a machine readable card encoded with a unique identifier, literature describing the proper use and/or benefit of said drug.

4. A method according to claim 1 wherein said deposit account is a temporary deposit account created and funded in an amount for reimbursing said pharmacy for the charges incurred in providing said drug sample to said patient.

5. A method according to claim 1 comprising funding said deposit account with a service fee to be paid to the pharmacy in addition to said charge for said drug sample in response to said card being read by a card reader linked to said insurance company payment processing system.

6. A method according to claim 1 comprising obtaining from said patient when said drug sample is distributed to said patient, personal data sufficient to enable receipt from said patient of information indicative of said patient's experience with said drug.

7. A method of distributing a prescription drug sample to a consumer through a pharmacy, the method comprising the steps of;

preparing a plurality of machine readable cards each of which is encoded with a unique identifier, preparing a plurality of packages each of which comprises one of said cards, literature describing a prescription drug, and patient instructions for participating in a test or questionnaire;

distributing to a drug prescriber at least one of said plurality of packages, wherein said drug prescriber distributes at least one of said plurality of packages to a patient to whom a prescription for a sample of said drug is provided;

funding, by a computer, a plurality of temporary deposit accounts with an insurance company payment processing system, each of said temporary deposit accounts having an identifier in correspondence with one of said unique identifiers, said insurance company payment processing system being accessible by said pharmacy for obtaining payment for drugs dispenses to customers insured by an insurance company that pays claims through said insurance company payment processing system; and reimbursing said pharmacy from said funded deposit account for its charge for said drug sample in response to said card being read by a card reader linked to said insurance company payment processing system, wherein said funded deposit account is only accessible by said pharmacy after successful completion of said test or questionnaire by said patient.

8. A method according to claim 7 further comprising, interpreting said unique identifier in response to said card being read by a card reader, and producing an authorization for reimbursing said pharmacy for said charge for said drug sample corresponding to said unique identifier before reimbursing said pharmacy for said charge for said drug sample.

9. A method according to claim 7 comprising funding said deposit account with a service fee to be paid to the pharmacy in addition to said charge for said drug sample in response to said card being read by a card reader linked to said insurance company payment processing system.

10. A method according to claim 7 comprising obtaining from said patient when said drug sample is distributed to said patient, personal data sufficient to enable receipt from said patient of information indicative to said patient's experience with said drug, and communicating with said patient after said sample is dispensed to said patient for determining said patient's experience with said drug.

* * * * *